United States Patent [19]

Thompson

[11] 4,291,228

[45] Sep. 22, 1981

[54] DETECTOR SHAPE AND ARRANGEMENT FOR POSITRON ANNIHILATION IMAGING DEVICE

[75] Inventor: Christopher J. Thompson, Montreal, Canada

[73] Assignee: Montreal Neurological Institute, Montreal, Canada

[21] Appl. No.: 70,372

[22] Filed: Aug. 28, 1979

[30] Foreign Application Priority Data

Jun. 19, 1979 [CA] Canada ................................. 330087

[51] Int. Cl.³ .............................................. G01T 1/20
[52] U.S. Cl. ................................. 250/363 S; 250/367
[58] Field of Search ................ 250/361 R, 363 S, 367, 250/445 T, 483, 487

[56] References Cited

U.S. PATENT DOCUMENTS 3,225,193 12/1965 Hilton et al. ......................... 250/367
3,621,256 11/1971 Cacheux et al. .................... 250/370
4,180,737 12/1979 Kingsley .......................... 250/445 T Primary Examiner—Alfred E. Smith
Assistant Examiner—Janice A. Howell
Attorney, Agent, or Firm—Beveridge, DeGrandi, Kline & Lunsford

[57] ABSTRACT

A circular array of detectors is used for detecting coincident events and the point of annihilation in a positron annihilation process in a selected plane wherein the output from the detectors is processed in a computer to provide image reconstruction for the selected plane. Bismuth germanate is shown to be more efficient than previously used detectors and the adaption of trapezoidal shape for the detectors enables more efficient utilization of the photons produced in the process. The use of absorbing metal reducing plugs between adjacent detectors may be used to decrease the aperture function of the detectors for low angles of incident radiation.

10 Claims, 5 Drawing Figures

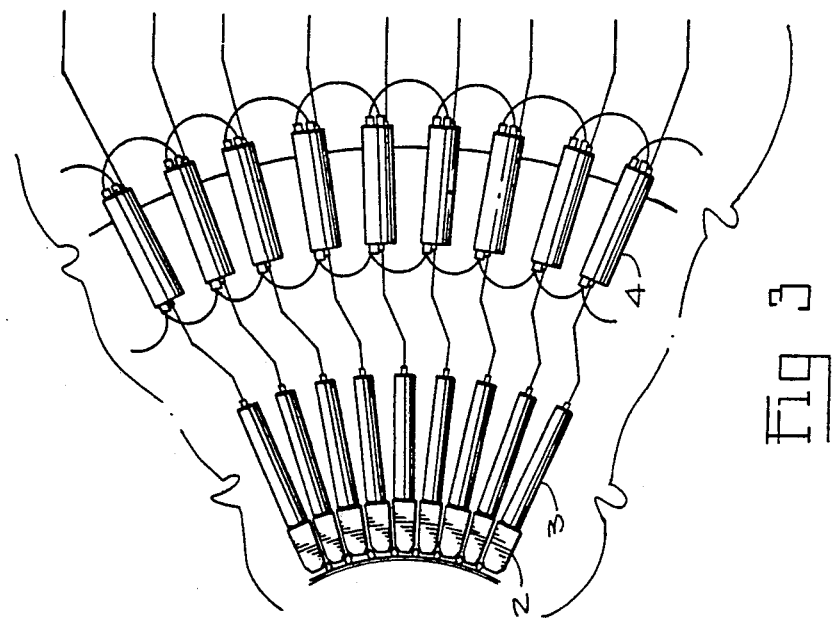
Fig 3
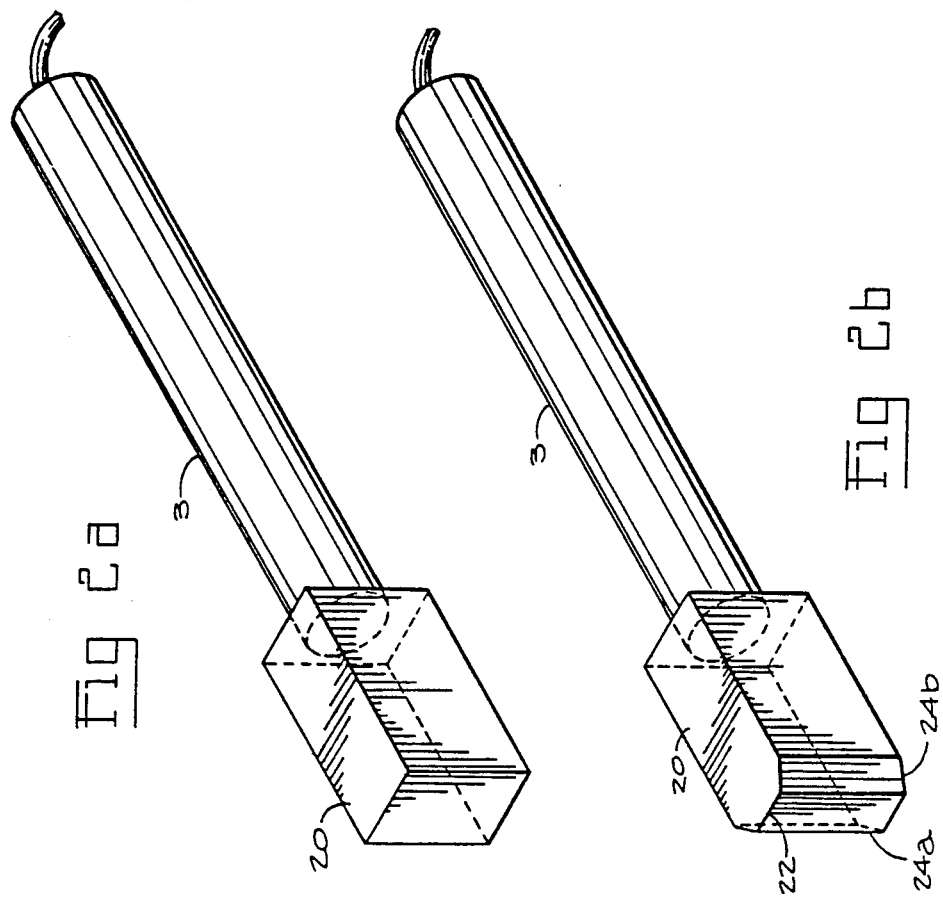
Fig 2a
Fig 2b

DETECTOR SHAPE AND ARRANGEMENT FOR POSITRON ANNIHILATION IMAGING DEVICE

BACKGROUND OF THE INVENTION

1. Field of the Invention

This invention relates generally to positron emission tomography and more particularly to devices which use an array of scintillation detectors to detect the annihilation radiation from positron disintegration and use this information to reconstruct an image of the distribution of positron emitting isotopes within a body.

2. Description of the Prior Art

Positron emission tomography is a technique for measuring the concentration of a positron emitting isotope through a sectional plane through the body. Normally the isotope is used to label a substance which circulates with the blood and which may be absorbed in certain tissues. The technique allows the actual concentration in the slice to be determined after suitable calibration of the device.

Certain isotopes decay by emitting a positively charged particle with the same mass as the electron (positron) and the neutrino from the nucleus. In this process one of the protons in the nucleus becomes a neutron, so that its atomic number goes down while its atomical weight remains constant. This positron is ejected with a kinetic energy of up to 2 Mev depending on the isotope and loses this energy by collisions while travelling a distance of up to a few mms in water. When it has reached thermal energies it interacts with an electron and they mutually annihilate one another. The rest mass of the 2 particles is transformed into 2 gamma rays of 511 Kev which are emitted at 180° in the 'center of mass' coordinates of the original particles. The 2 gamma rays may be detected by suitable devices. If these devices measure the energy of the gamma rays at about 511 Kev and register this energy almost simultaneously it may be assumed that the origin of the radiation is on a straight line between the two detectors. Several detectors may be used in an arrangement so that many coincident events may be imaged during the same time interval. Then the information from these detectors is processed by a computer using image reconstruction techniques in order to find the location of distribution of positron emitting isotope.

A device for imaging positron annihilation radiation requires all of the following basic parts:

(1) A number of detectors arranged in a precise geometrical pattern. These detectors are normally scintillation detectors disposed in one or several planes, and these detectors are normally arranged in a polygonal pattern on the circumference of a common circle. Scintillation detectors emit a light flash each time they absorb gamma radiation which may or may not arise from the mutual annihilation of a positron and an electron. The intensity of the light flash is proportional to the gamma ray energy.

(2) The device, using scintillation detectors, must contain a means of converting the light flashes to electrical charge pulses whose amplitude is proportional to the light intensity. This may be a photomultiplier or solid state device.

(3) The device must contain a means of determining that any charge pulse could have arisen from a gamma ray whose energy was approximately equivalent to the mass of the electron at rest (e.g. 511 Kev).

(4) The device must have an electronic circuit capable of determining that two and only two detectors each recorded gamma rays of appropriate energy within a short time interval (coincidence resolving time). These detectors are said to have recorded a 'coincident event'.

(5) The device must have an electric circuit which determines which two detectors, out of the many possible combinations, recorded the so-called 'coincident event.'

(6) The device must have a memory in which it can record how often each pair of detectors record a 'coincident event.' The memory may be part of a random access memory of a general purpose computer.

(7) The device is required to use an algorithm through which the information in the memory may be transformed into an image of the distribution of positron annihilation in a cross-section surrounded by the detectors. The sequence of steps described by this algorithm may be programmed into a general purpose computer.

Accordingly, it is an object of this invention to provide a positron annihilating imaging device which has an efficiency greater than previously existing devices in its class.

Another object of the invention is to prevent gamma rays entering a given detector which are not absorbed because of the imperfect stopping power of the detector, from reaching another detector, so that all or part of the energy of the gamma rays is dissipated in a second detector.

A further object of the invention is to increase the efficiency of the individual detectors, in a positron annihilation imaging device, to radiation which is not incident normal to the detectors' face. Since any detectors may be in coincidence most of the radiation falling on the detectors is not incident normally on it but at an angle which is significantly different from 90°.

A further object of this invention is to enable heavy metal objects to be placed in-between the detectors, in a positron annihilation device, in such a way as to decrease the apparent widths (aperture functions) of the detectors, which, while reducing the efficiency of individual detectors, reduces their aperture functions allowing a subsequent increase in spatial resolution.

In accordance with an aspect of this invention, the detectors are arranged in planes and around the circumference of common circles.

In accordance with an aspect of this invention, the detectors may be basically trapezoidal in shape with the smaller face of the trapezoid being disposed on a circle extending around the body undergoing examination. The outer face of the trapezoid which is larger, is in optical contact with the face of an associated photomultiplier tube or other device which can convert light into an electric pulse.

In accordance with another aspect of this invention, the detectors are made from bismuth germanate, a dense scintillating crystal which is approximately 2.5 times more efficient than sodium iodide crystals.

In accordance with another aspect of this invention, the bismuth germanate detector crystals are separated by tungsten septa which decreases the probability of the penetration of gamma rays from one detector to the other.

In accordance with another aspect of this invention, the shape of the detector crystals may be further modified by cutting the corners of the front face of the detectors at an angle of 45° giving the front of the detector a somewhat pointed shape.

In accordance with another aspect of this invention, between the shaped detector fronts may be inserted a heavy metal diamond shaped plug which can be removed at will. The purpose of this plug is to change the aperture function of the detectors allowing a trade-off between high efficiency and high spatial resolution.

In accordance with another object of this invention, the placement of the above-mentioned heavy metal objects and their shape is such as not to impede the intensity of incident radiation for angles up to about 30° from the perpendicular to the front face.

In accordance with the foregoing aspects of the invention, there is provided:

A scintillation detector for use in the detection of annihilation radiation in a positron disintegration process, said detector comprising a right prism of bismuth germanate, one end face of said prism being in optical contact with a light-amplifying device and the other end face of said prism being exposed to said radiation, at least the side surfaces of said prism having a light reflective coating thereon.

A preferred embodiment of the invention will now be described with reference to the accompanying drawings, in which:

FIGS. 2a and 2b are isometric views of a detector-crystal and photomultiplier combination, without and with 45° corner cuts on the face of the crystal, respectively;

FIG. 3 is a representative portion of one plane of a circular array of detectors, associated photomultipliers and local amplifiers.

Figure 1:
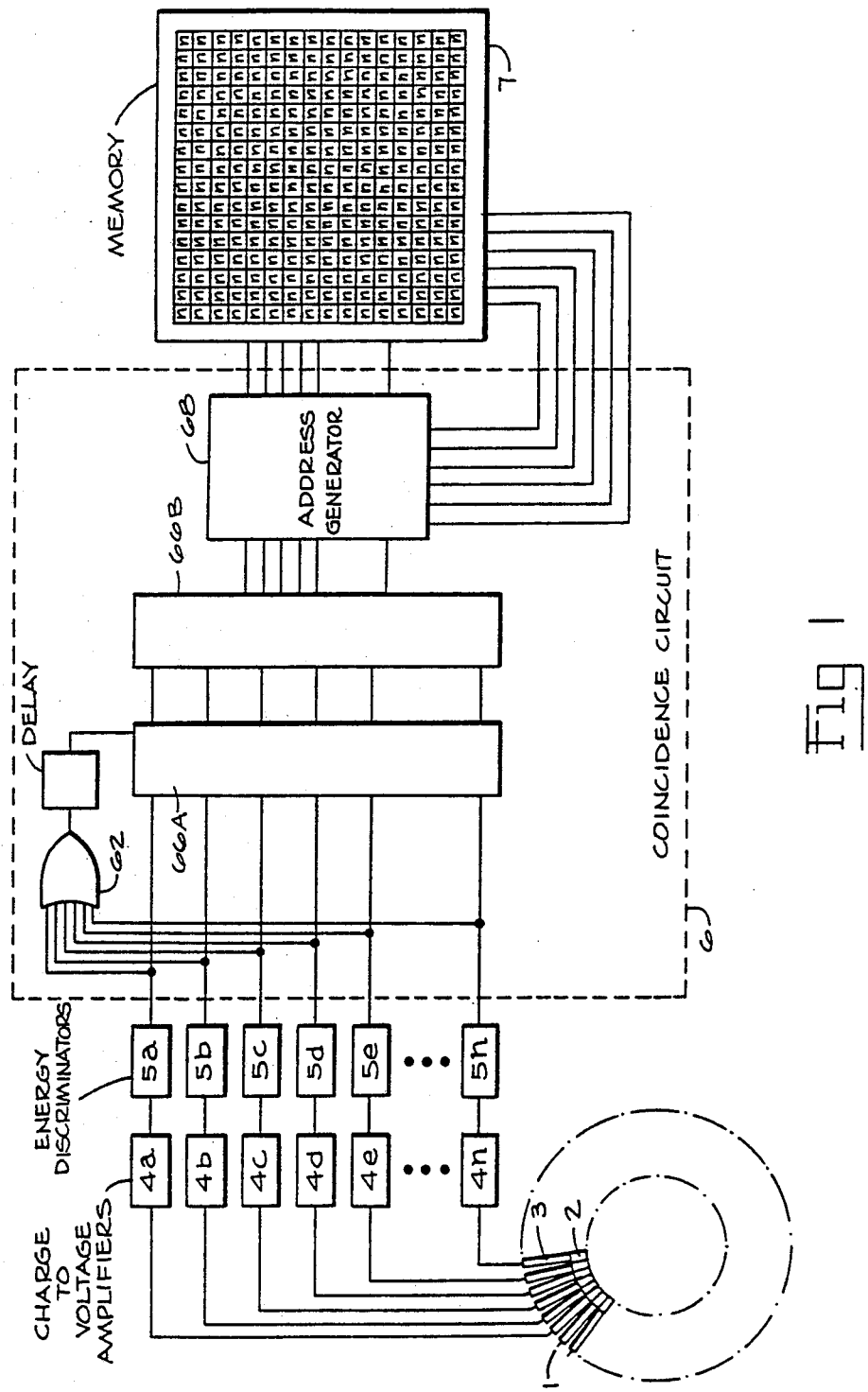
FIG. 1 is a block diagram showing the interconnections between the main components.

Referring now to FIG. 1, there is shown a ring 1 of cyrstal detectors 2, associated photomultipliers 3 each one of which is connected to an associated charge-to-voltage amplifier 4a, 4b–4n. The respective amplifers 4 are connected to energy discriminators 5a, 5b–5n, the outputs of which are connected into a coincidence circuit 6 and applied on OR gates which is indicated at 62. The amplifiers 4 shape the signal from the photomulitipliers 3 to provide an input suitable for the discriminators 5 each of which produce a timing pulse for each energy selected event. A suitable resolving time delay 64 is inserted between the gates 62 and the storage registers 66A and 66B whose output are connected to address registers 68. The coincidence circuit 6 provides input for a memory 7.

Referring now to FIG. 2a, which is a view of a bismuth germinate scintillation crystal 20, showing the basic trapezoidal shape, and a photomultiplier 3 attached to the rear face of the crystal.

FIG. 2b, is similar to FIG. 2a but wherein the lesser 22 face of the trapezoid cut away on opposite sides to form flats 24a and 24b. The flats may be formed at 45° to the face of the crystal 20.

The crystals 20 are painted white so that all the light from each scintillation is reflected from all sides except the rear face through which it emerges to be recorded by the photomultipliers 3. The shaping of the front face of the crystals 20 somewhat reduces the efficiency for normally incident radiation, it greatly increases the efficiency for radiation at angles of incidence of up to 30°, thereby improving the overall efficiency of the device.

FIG. 3 shows a portion of a circular array of detectors 2, photomultipliers 3 and amplifiers 4. It will be observed that the detectors 2 may be provided with separators and/or heavy metal plugs therebetween and these will be discussed in more detail in connection with FIG. 4.

Figure 4:
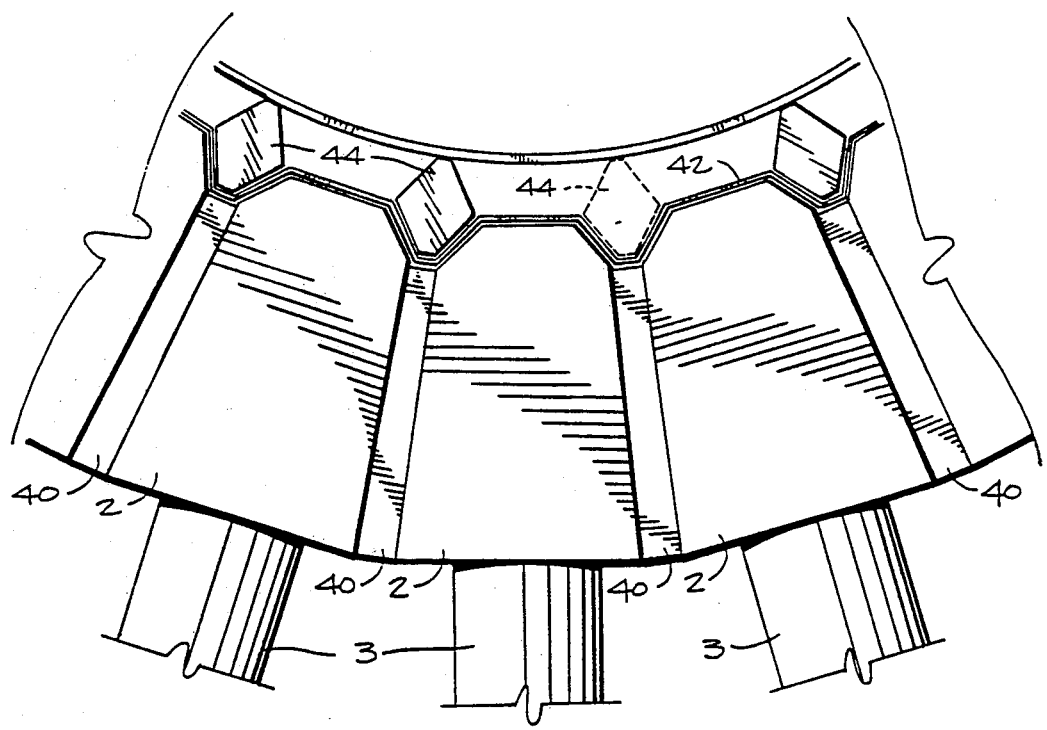
FIG. 4 is a representative portion of one plane of a circular array of detectors with shaped crystals and optional shields and absorbent plugs.

Referring now to FIG. 4, there is shown a portion of a circular array of detectors 2 and photomultipliers 3. While FIG. 4 and FIGS. 1 and 3 indicate a single plane of circularly arranged detectors 2, photomultipliers 3 and amplifiers 4, it is to be understood that there may be two or more such planes containing similar components. As previously stated, the detectors are painted white (or some other reflective coating) on all surfaces except for that area in contact with the photomultipliers. Provision is made for inserting, at will, heavy metal, such as lead or tungsten, plugs 44 between the detectors. The plugs 44 serve to decrease the apparent widths (aperture functions) of the detectors. While this reduces the collection area of individual detectors it provides an increase in spatial resolution. While FIG. 4 indicates detectors 2 having substantially trapezoidal shape, that is with the smaller inner end facing the centre of the array 1 and the larger outer end facing the photomultipliers 3, and with parallel spacers or septa 40 therebetween, the detectors 2 may be of constant cross section and the spacers or septa 40 of wedge shape.

The septa may be eliminated entirely, of course, as they are only effective if they are much more dense than the scintillation crystal.

It will be observed that the detectors shown in FIG. 4 have the 45° corners formed thereon, as discussed previously in connection with FIG. 2b. The 45° angle is not, of course, critical.

The separators 40, which may be formed of tungsten, may also serve as part of a light-tight enclosure for the individual detector crystals.

The front surface of the light sealed enclosure is made out of thin foil 42 of stainless steel or similar material which is bent to follow the contour of the individual crystals.

The detectors may also be of modular form for ease of replacement. In this case, each unit would be separately light-tight.

The individual detector crystals 2 can be held permanently in an assembly or in another embodiment, they can be made individually demountable so that the photomultiplier and crystal assembly can be replaced as a unit for servicing.

The individual lead width reducing plugs 44 are mounted on another piece of stainless steel in the shape of a band which can be pressed into place and is retained on the body of the light sealed enclosure.

The advantages of the invention can be summarized as follows:

A scintillation detector formed of bismuth germanate is more dense than previously used scintillation material, e.g. sodium iodide.

Since coincidence counting efficient depends on the square of the individual detector efficiency an overall improvement factor of 4–10 is possible depending on the crystal size and orientation.

Placing the detectors in a circular plane gives rise to a perfectly symmetrical detector arrangement which uniformly surrounds the body with radiation detecting material. This arrangement is suitable for use in an image reconstruction algorithm.

Placing the detectors uniformly about a circle in the tightest possible configuration prevents either of a pair of gamma rays in that plane escaping from the plane without penetrating one of the detectors, thereby maximizing the probability of detection.

The basic trapezoidal shape of the detectors is optimum for gamma rays approaching detectors at normal incidence and at angles very close to 90°.

The basic trapezoidal shape is clearly more efficient than the right circular cylinder used in the prior art. It is also more efficient than a rectangular shape used in the recent prior art in that more of the volume surrounding the patient is filled with detecting material rather than being wasted.

Much of the radiation incident of these detectors is from angles up to 30° on either side of normal incidence. For a 42 cm diameter ring radiation at 30° falls outside the 25 cm area used in image reconstruction. Other angles, diameters, and areas would be appropriate for other embodiments. The path travelled by this radiation is much less than the possible 3 cms of the detecting material available to the photons which are incident normally on the detector face. In order to maintain the spatial resolution of the device as good at the periphery as it is in the center, it is necessary to prevent radiation which should have been absorbed in a detector in which it is first incident from being transmitted to a neighboring detector. This is achieved by placing a tungsten septum between the detectors. The tungsten absorbs the stray radiation to a greater extent that the bismuth germanate, thus maintaining higher spatial resolution towards the edge of the image than is possible without the septa.

The detector shape is further optimized for off normal incident radiation by shaping the front face cutting back 2 sides at 45°. Although this somewhat reduces the detection efficiency for normally incident radiation, it greatly increases the efficiency for radiation at angles up to 30°, thereby improving the overall efficiency of the device.

The shape just described also has the effect of minimizing the effect of the lower spatial resolution at the periphery of the image by exposing a greater area of the detector face to radiation which is off normal incidence.

The gap in-between the front faces of adjacent detectors when filled with a removable heavy metal plug has the effect of decreasing the aperture function of each detector for all angles of radiation up to 30° from normal incidence.

The heavy metal plug in front of the detectors can be placed or removed at will allowing efficiency to be traded off for spatial resolution appropriate to the scan being performed.

The shape of the detectors allows the point at which half the incident radiation is absorbed (approximately 8 to 9 mms) from the point of incidence of tha gamma ray to remain approximately constant independent of the incident angle.

The effect just described can be used in the reconstruction algorithm in such a way that the detectors are said to be on a circle of diameter approximately 1.7 cms more than the actual diameter, thus compensating for the effective penetration depths of 50% of the gamma rays incident on the detectors.

Recessing the heavy metal plugs into the detectors allows the maximum amount of absorbing material to be placed between detectors to reduce their aperture function without reducing the detectors' view of radiation of up to 30°.

The embodiments of the invention in which an exclusive property or privilege is claimed are defined as follows:

1. A scintillation detector for use in the detection of annihilation radiation in a positron disintegration process, said detector comprising an array of detector elements, each element being a crystal of bismuth germanate, each crystal having a first end face of a first area and a second, opposite and parallel end face of a second area larger than said first area, at least the side surfaces of each crystal having a light reflective coating thereon, said plurality of detector elements being disposed in a common plane, equally spaced apart about a common circle with each detector element having its said first end face directed to and spaced apart from the center of said circle for exposure to radiation from points within said circle and within said common plane and adjacent planes, allowing radiation from the points to pass into said first end face of each of said crystals, through each of said crystals, and out said second end face of each of said crystals; and a light amplifying device in optical contact with said second end face of each of said crystals.

2. A scintillation detector as in claim 1 wherein each said crystal is trapezoidal in one plane.

3. A scintillation detector as in claim 2 wherein each said crystal has two rectangularly shaped facets disposed adjacent to respective opposing sides and said first end face.

4. A scintillation detector as in claim 3 wherein said facets are disposed at approximately 45° to the axis of symmetry of said crystal.

5. An array of detectors as defined in claim 2 wherein said trapezoidal configuration defines a pair of non-parallel sides, said non-parallel sides being located substantially radially with respect to said common circle.

6. A detector as defined in claim 2 further including a plurality of heavy metal shields disposed between adjacent detector elements.

7. A detector as in claim 5 further including a plurality of heavy metal shields disposed between adjacent detector elements.

8. A detector as in claim 7 further including a plurality of heavy metal plugs placed between and abutting opposing facets on the adjacent detector elements, said plugs leaving the said first end face unobstructive to incident radiation.

9. A scintillation detector as in claim 1 wherein each said crystal has two rectangular shaped facets disposed adjacent to respective opposing sides and said first end face.

10. A scintillation detector as in claim 9 wherein said facets are disposed at approximately 45° to the axis of symmetry of said crystal.

* * * * *